(12) United States Patent
Chung

(10) Patent No.: US 11,945,001 B2
(45) Date of Patent: Apr. 2, 2024

(54) FAT SCREENING DEVICE

(71) Applicant: Hsing-Chi Medical Ltd., New Taipei (TW)

(72) Inventor: Meng-Wen Chung, New Taipei (TW)

(73) Assignee: HSING-CHI MEDICAL LTD., New Taipei (TW)

( * ) Notice: Subject to any disclaimer, the term of this patent is extended or adjusted under 35 U.S.C. 154(b) by 414 days.

(21) Appl. No.: 17/201,460

(22) Filed: Mar. 15, 2021

(65) Prior Publication Data

US 2022/0241469 A1 Aug. 4, 2022

(30) Foreign Application Priority Data

Feb. 3, 2021 (CN) .......................... 202120313927.6

(51) Int. Cl.
*B07B 1/46* (2006.01)

(52) U.S. Cl.
CPC ... *B07B 1/4609* (2013.01); *A61M 2202/0021* (2013.01); *A61M 2202/005* (2013.01); *B07B 2201/02* (2013.01); *B07B 2230/01* (2013.01)

(58) Field of Classification Search
CPC ............... B07B 1/00; A61M 2202/005; A61M 2202/0021
USPC ........................ 604/406; 209/12.1, 13, 17, 18
See application file for complete search history.

(56) References Cited

U.S. PATENT DOCUMENTS

| | | | | |
|---|---|---|---|---|
| 2,892,002 A * | 6/1959 | Summers, Jr. | ......... | B01J 8/0278 |
| | | | | 209/474 |
| 4,028,229 A * | 6/1977 | Dell | ......................... | B03D 1/22 |
| | | | | 210/221.1 |
| 4,157,951 A * | 6/1979 | Park | ........................ | B03B 5/623 |
| | | | | 209/159 |
| 4,624,791 A * | 11/1986 | Ferriss | ...................... | C02F 1/28 |
| | | | | 95/170 |
| 7,632,416 B2 * | 12/2009 | Levitt | .................. | B01D 29/908 |
| | | | | 210/791 |

FOREIGN PATENT DOCUMENTS

| | | | | | |
|---|---|---|---|---|---|
| CN | 111214888 B | * | 4/2022 | ............ | B01D 36/00 |
| KR | 100387992 B1 | * | 1/2001 | | |
| KR | 100387992 B1 | * | 6/2003 | | |

* cited by examiner

*Primary Examiner* — Terrell H Matthews
(74) *Attorney, Agent, or Firm* — MUNCY, GEISSLER, OLDS & LOWE, P.C.

(57) ABSTRACT

A fat screening device includes a cylinder, and a sieve basket. The cylinder includes a feed inlet, an air outlet, a bottom water outlet, and an accommodating space. The accommodating space is in communication with the feed inlet, the air outlet, and the bottom water outlet. The feed inlet is configured to receive a mixture, the bottom water outlet is disposed at a bottom of the cylinder, the accommodating space is configured to accommodate water and fat resulting from stratification of the mixture, and the bottom water outlet is configured to discharge the water. The sieve basket covers the feed inlet and is arranged separately from the air outlet. The sieve basket is configured to screen the mixture to discharge the water and the fat into the accommodating space.

17 Claims, 5 Drawing Sheets

FAT SCREENING DEVICE

CROSS-REFERENCE TO RELATED APPLICATION

This non-provisional application claims priority under 35 U.S.C. § 119(a) to Patent Application No. 202120313927.6 filed in China, P.R.C. on Feb. 3, 2021, the entire contents of which are hereby incorporated by reference.

BACKGROUND

Technical Field

The instant disclosure relates to a screening device, and in particular, to a fat screening device.

Related Art

General fat transplantation is to first remove autologous fat by using a liposuction technology and then transplant collected fat to a specific part through injection after screening and separation. Common surgical methods include high-frequency current fat-cutting, dermal fat removal, ultrasonic fat-cutting, mechanical vibration, and the like. However, a traditional fat collecting method is to first collect the removed fat into a container and then extract the fat from the container for transplantation. However, inconsistent quality of the removed fat may result in a low survival rate of the fat.

SUMMARY

In view of the above, some embodiments of the instant disclosure provide a fat screening device.

A fat screening device in an embodiment of the instant disclosure includes a cylinder, and a sieve basket. The cylinder includes a feed inlet, an air outlet, a bottom water outlet, and an accommodating space. The accommodating space is in communication with the feed inlet, the air outlet, and the bottom water outlet. The feed inlet is configured to receive a mixture, the bottom water outlet is disposed at a bottom of the cylinder, the accommodating space is configured to accommodate water and fat resulting from stratification of the mixture, and the bottom water outlet is configured to discharge the water. The sieve basket covers the feed inlet and is arranged separately from the air outlet. The sieve basket is configured to screen the mixture to discharge the water and the fat into the accommodating space.

Based on the above, the fat screening device in the embodiments of the instant disclosure effectively improves quality and a survival rate of collected fat through a gravity separation principle and screening of the cylinder and the sieve basket, which is adapted for separating and collecting fat cells with a high survival rate from living tissues for fat transplantation.

DETAILED DESCRIPTION

Figure 1:
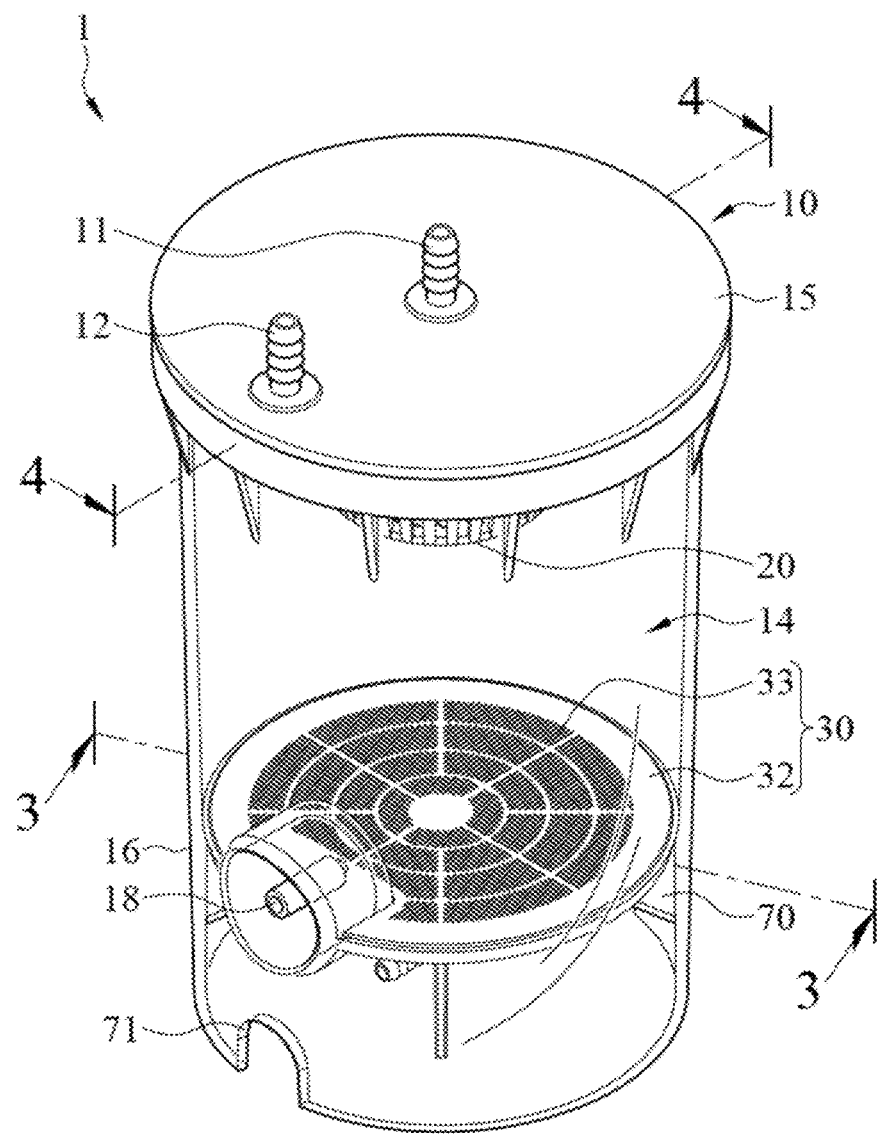
FIG. 1 is a three-dimensional view of a fat screening device according to an embodiment of the instant disclosure.

Embodiments of the instant disclosure are described in detail below, and illustrated with the drawings. The specification provides many specific details for readers to have relatively complete understanding of the instant disclosure. However, the instant disclosure may still be implemented with some or all specific details omitted. The same or similar elements in the drawings are represented by the same or similar symbols. It is particularly noted that the drawings are merely for illustration, and do not represent actual sizes or quantities of components. Some details may not be completely drawn for concision of the drawings.

Figure 2:
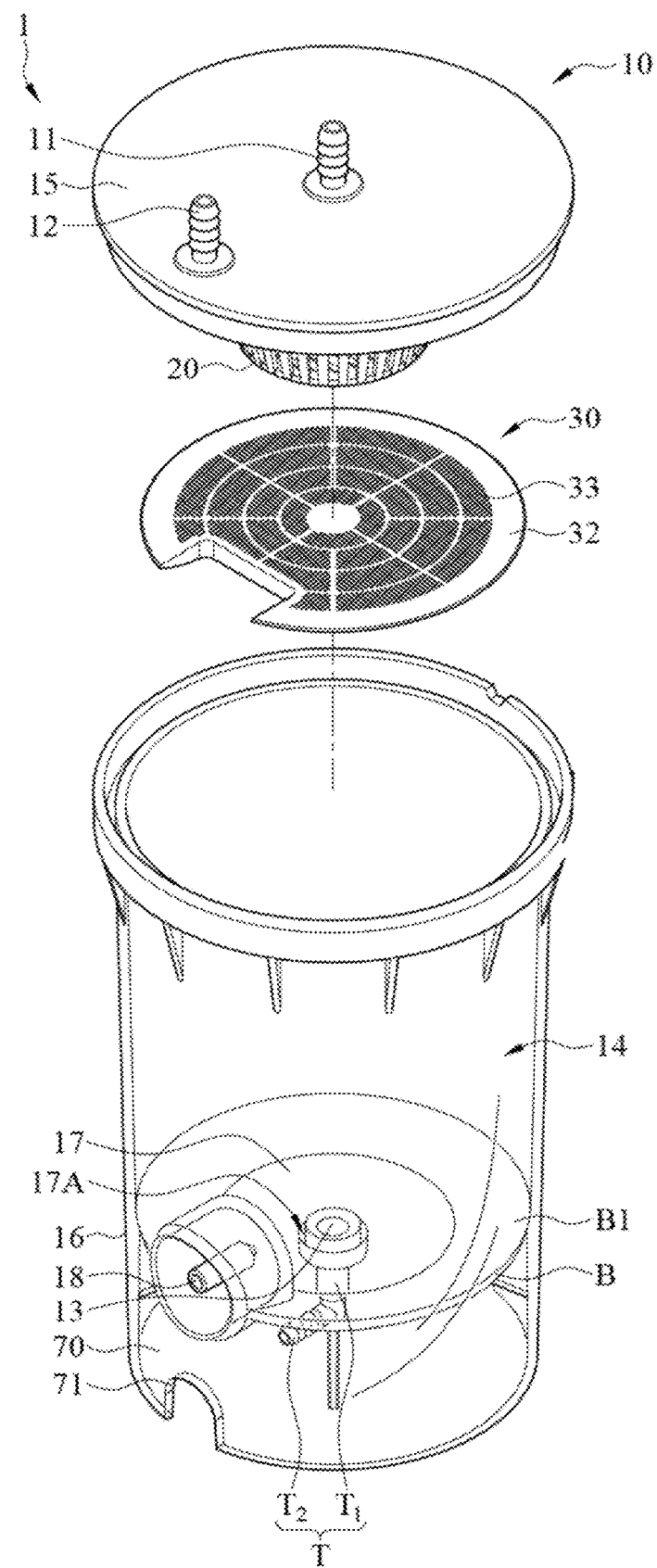
FIG. 2 is a three-dimensional exploded view of a fat screening device according to an embodiment of the instant disclosure.
Figure 3:
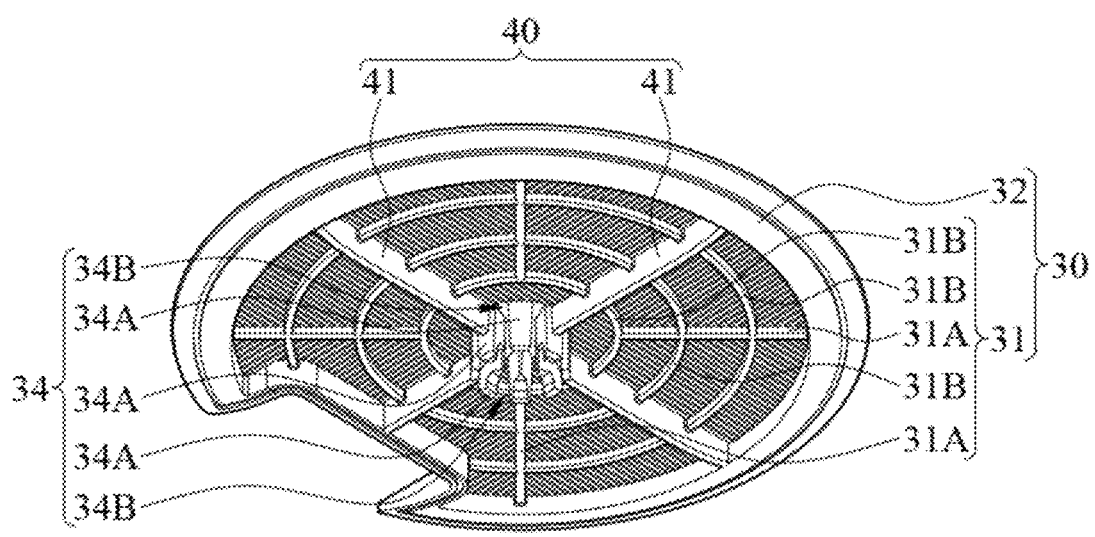
FIG. 3 is a three-dimensional view of a filter mesh according to an embodiment of the instant disclosure.

FIG. 1 is a three-dimensional view of a fat screening device according to an embodiment of the instant disclosure. FIG. 2 is a three-dimensional exploded view of a fat screening device according to an embodiment of the instant disclosure. FIG. 3 is a three-dimensional view of a filter mesh of the fat screening device in FIG. 2. FIG. 2 is a top-down view of the filter mesh, and FIG. 3 is a bottom-up view of the filter mesh. Referring to FIG. 1 to FIG. 3, a fat screening device in an embodiment of the instant disclosure includes a cylinder 10 and a sieve basket 20. The sieve basket 20 is assembled in the cylinder 10. In some embodiments, the cylinder 10 and the sieve basket 20 may be integrally formed. The cylinder 10 includes a feed inlet 11, an air outlet 12, a bottom water outlet 13, and an accommodating space 14. The accommodating space 14 is formed by a top 15, a side wall 16, and a bottom 17 of the cylinder 10. The accommodating space 14 is in communication with the feed inlet 11, the air outlet 12, and the bottom water outlet 13. Two sides of the side wall 16 are respectively connected to the top 15 and the bottom 17.

Figure 4:
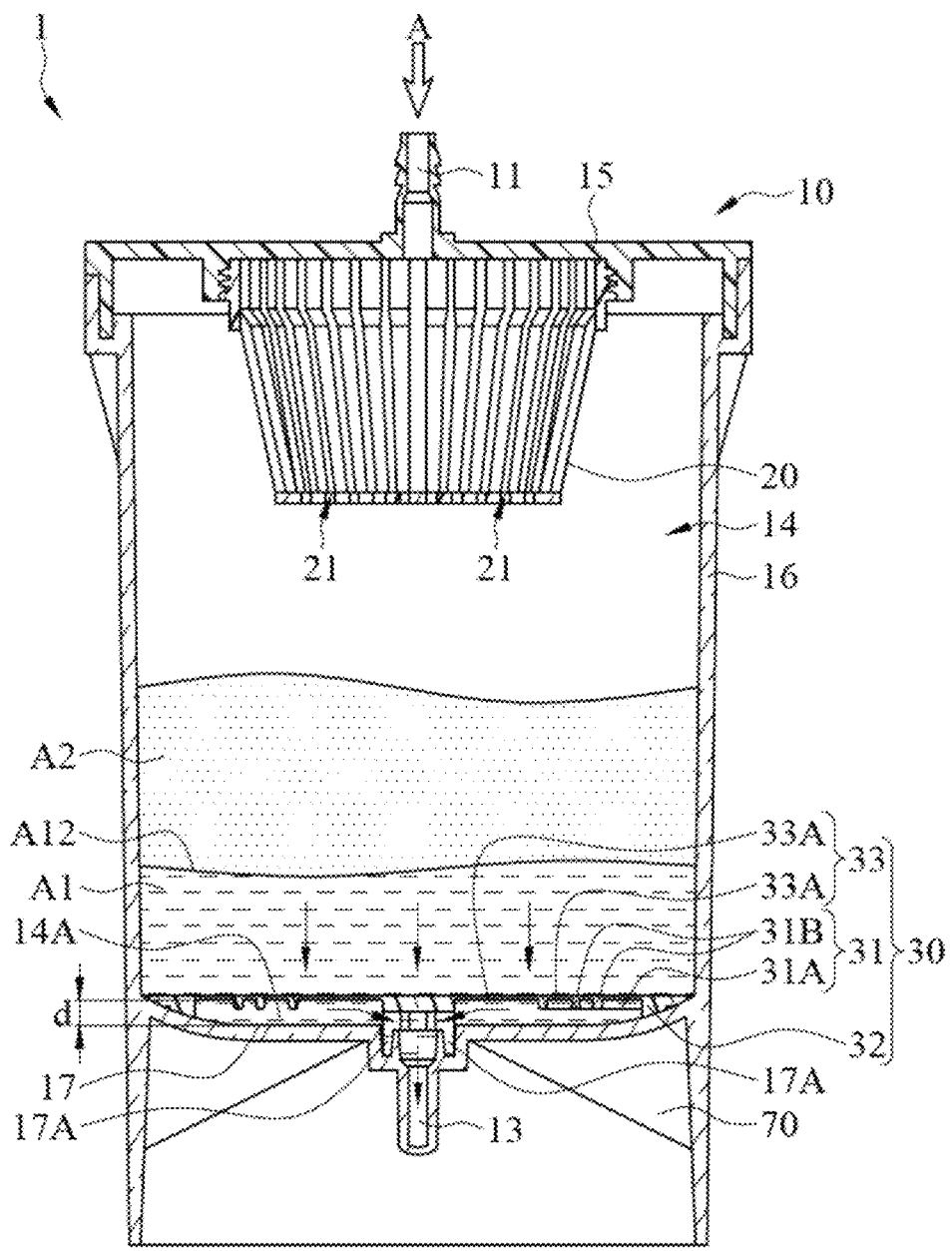
FIG. 4 is a cross-sectional view of a fat screening device according to an embodiment of the instant disclosure.

FIG. 4 is a cross-sectional view of a fat screening device according to an embodiment of the instant disclosure. Referring to FIG. 1 to FIG. 4, in this embodiment, the feed inlet 11 is oriented toward the sieve basket 20 and disposed at the top 15 of the cylinder 10. For example, the feed inlet 11 is disposed at a center of the top 15, but the instant disclosure is not limited thereto. The cylinder 10 receives a mixture A through the feed inlet 11, and the mixture flows into the sieve basket 20. The screened mixture A flows into and is stored in the accommodating space 14. For example, the sieve basket 20 is arranged in the accommodating space 14 and covers a lower part of the feed inlet 11. The sieve basket 20 screens the mixture A to discharge the screened mixture A to the accommodating space 14. The mixture A includes water A1 and a small volume of fat A2. In some embodiments, a lateral surface and a bottom surface of the sieve basket 20 are provided with a plurality of sieve openings 21. In at least one embodiment, a size the plurality of sieve openings 21 ranges from 1 mm to 4 mm, but the instant disclosure is not limited thereto.

Since the screened water A1 and fat A2 have hydrophilicity and density values different from each other, the screened mixture A is automatically separated into two layers of fluids by gravity when being stored in the accommodating space 14, and the fluids intersect at an interface A12. In this way, the screened water A1 and fat A2 form layered structures separated from each other and are stored in the accommodating space 14.

In order to guide the mixture A to smoothly flow into the cylinder 10, an air outlet 12 is provided at the top 15 of the cylinder 10 for discharging gas in the accommodating space 14, such as air. For example, the air outlet 12 is provided at a periphery of the top 15 and deviates from a center, that is, an orthographic projection of the air outlet 12 on the top 15 does not overlap an orthographic projection of the sieve basket 20 on the top 15, so that the air outlet 12 and the sieve basket 20 are arranged alternately with each other to prevent the fat or the water in the sieve basket 20 from being discharged out of the cylinder 10 through the air outlet 12, thereby ensuring that only the gas in the accommodating space 14 is discharged out of the cylinder 10 through the air outlet 12. In this way, the accommodating space 14 of the cylinder 10 enters a negative pressure state after at least a part of the gas is discharged, so that the mixture A can flow into the cylinder 10 smoothly.

Figure 5:
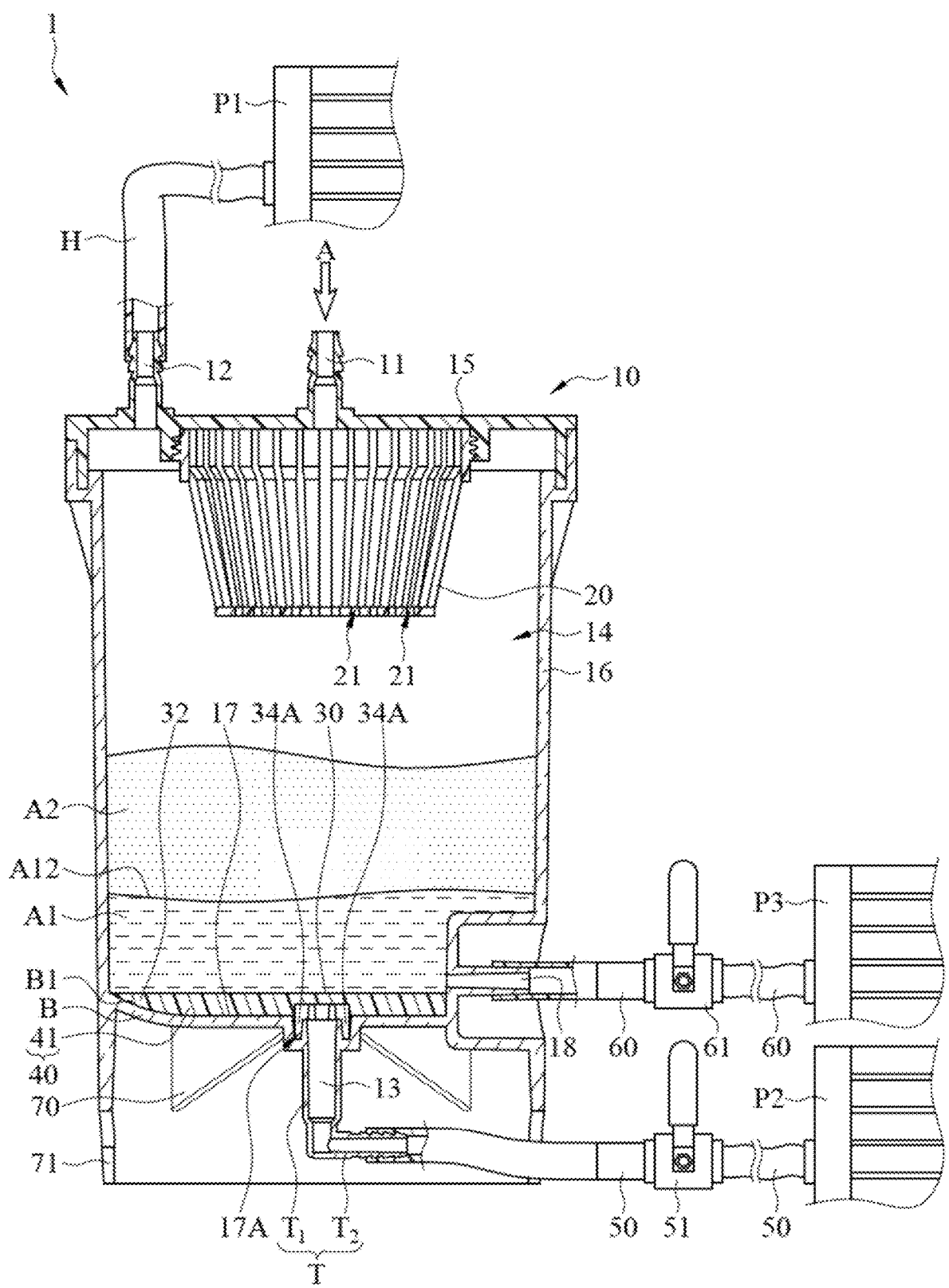
FIG. 5 is another cross-sectional view of a fat screening device according to an embodiment of the instant disclosure.

FIG. 5 is another cross-sectional view of a fat screening device according to an embodiment of the instant disclosure. As shown in FIG. 5, in this embodiment, in order to increase a flow rate of the mixture A in the cylinder 10, the fat screening device 1 may be optionally equipped with a vacuum pump P1, which is in communication with the air outlet 12 of the cylinder 10 through a negative pressure pipe H to draw and discharge the gas in the accommodating space 14, but the instant disclosure is not limited thereto.

In addition, the bottom water outlet 13 is disposed at the bottom 17 of the cylinder 10. For example, the bottom water outlet 13 is disposed at a center of the bottom 17, but the instant disclosure is not limited thereto. Since fat A2 in the accommodating space 14 is suspended at an upper layer and away from the bottom 17, the cylinder 10 can discharge the water A1 adjacent to the bottom 17 out of the cylinder 10 through the bottom water outlet 13. In this way, the screened fat A2 is retained in the accommodating space 14 of the cylinder 10 for subsequent transplantation.

One of factors for successful fat transplantation is quality and a survival rate of collected fat cells. For example, since fat cells at a center of oversized cellulite after transplantation cannot easily absorb nutrients, a survival rate is relatively low. Alternatively, autologous tissues removed through liposuction are often accompanied by other components besides fat cells, for example, fibrous tissues rather than fat cells required for transplantation to a target site. Therefore, according to the above structure, the disclosure effectively improves the quality and the survival rate of the collected fat A2 through a gravity separation mechanism and a screening mechanism of the cylinder 10 and the sieve basket 20, which is adapted for separating and collecting fat cells with a high survival rate from living tissues for the fat transplantation, and has numerous functions and advantages as described above.

Referring to FIG. 1 to FIG. 4, in this embodiment, in order to prevent to-be-collected fat A2 from being discharged out of the cylinder 10 and improve quality and an amount of the fat A2, the accommodating space 14 of the fat screening device 1 is further configured with a filter mesh 30. The filter mesh 30 includes a circumferential plate 32 and a filter area 33 located in the circumferential plate 32. The filter area 33 has a plurality of filter holes 33A. The circumferential plate 32 and the filter area 33 may be integrally formed, or may be fixed to each other through bonding, locking, riveting, or the like. The circumferential plate 32 may be made of rigid materials such as plastic, metal, wood, or the like to ensure rigidity of the filter mesh 30.

Referring to FIG. 1 to FIG. 4 again, in this embodiment, a guide block B protrudes from a periphery of the bottom 17 of the cylinder 10. The guide block B is arranged annularly with the bottom water outlet 13 as a center, and the guide block B has a sloped guide surface B1. A cross section of the sloped guide surface B1 is arc-shaped and is inclined toward the bottom water outlet 13. The circumferential plate 32 of the filter mesh 30 geometrically matches the sloped guide surface B1, so that the circumferential plate 32 abuts against and is fixed to the sloped guide surface B1 of the guide block B. In this way, the filter area 33 of the filter mesh 30 covers the bottom water outlet 13 and is spaced apart from the bottom 17 of the cylinder 10 by a distance d, that is, a spacing 14A exists between the filter area 33 and the bottom 17 of the cylinder 10. In this way, the filter mesh 30 can filter the water A1 and discharge the water into the bottom water outlet 13, so that the fat A2 is retained in the accommodating space 14. In addition, as shown in FIG. 4, a direction directed by an arrow is a path through which the water A1 flows. After the water A1 flows through the filter mesh 30 through the filter holes 33A on the filter mesh 30, the water is discharged into the bottom water outlet 13 after passing through the spacing 14A. Therefore, the water A1 is not obstructed by the bottom 17 of the cylinder 10 on the path to the bottom water outlet 13 through the filter holes 33A, so that each filter hole 33A is fully utilized, thereby improving the drainage efficiency of the fat screening device 1.

Since the sloped guide surface B1 of the guide block B is inclined toward the bottom water outlet 13, the water A1 is guided by the sloped guide surface B1 to flow toward the bottom water outlet 13 when flowing through the sloped guide surface B1, thereby improving the drainage efficiency of the fat screening device 1. In some embodiments, the cross section of the sloped guide surface B1 may also be linear, which depends on usage requirements.

In at least one embodiment, a size of the plurality of filter holes 33A of the filter mesh 30 ranges from 100 μm to 400 μm, so that not only the water A1 can be smoothly discharged, but also the fat A2 larger than the filter holes 33A is retained in the accommodating space 14, thereby effectively increasing an amount of the collected fat A2. In some embodiments, a geometric shape of the filter mesh 30 may be a plate shape, a cone shape, or an arc shape, but the instant disclosure is not limited thereto.

Referring to FIG. 1 to FIG. 5, in this embodiment, a first assembling portion 17A is provided on the bottom 17 of the cylinder 10. The first assembling portion 17A is an annular buckling groove and surrounds the bottom water outlet 13. The first assembling portion 17A and the bottom 17 of the cylinder 10 may be integrally formed, or may be spliced together. A second assembling portion 34 is provided on a bottom surface of the filter mesh 30. The second assembling portion 34 includes a plurality of buckling claws 34A (includes six buckling claws herein, but the instant disclosure is not limited thereto) arranged annularly. A gap 34B exists between the buckling claws 34A, and the buckling claws are arranged in an equal proportion to each other. The second assembling portion 34 is correspondingly assembled to the first assembling portion 17A through buckling. In this way, in the fat screening device 1 of this embodiment, the second assembling portion 17A is correspondingly assembled to the first assembling portion 34, so that the filter mesh 30 can be firmly connected to the bottom water outlet 13, thereby ensuring a filtering effect of the filter mesh 30. In addition, through the gap 34B between the buckling claws 34A of the second assembling portion 34, the water A1 located in the spacing 14A can flow to the bottom water outlet 13 through the gap 34B, thereby improving the drainage efficiency of the fat screening device 1. In addition, since the buckling claws 34A of the second assembling portion 34 are arranged in an equal proportion to each other, a buckling force between the first assembling portion 17A and the second assembling portion 34 can be evenly distributed, so that a probability of product damage as a result of stress concentration is reduced.

In some embodiments, the first assembling portion 17A and the second assembling portion 34 may also be other assembling structures corresponding to each other. For example, the first assembling portion 17A and the second assembling portion 34 are locking structures, riveting structures, bonding structures, or the like corresponding to each other. In addition, structural geometry of the first assembling portion 17A and the second assembling portion 34 may also be transposed.

Referring to FIG. 1 to FIG. 5, the distance d between the filter area 33 of the filter mesh 30 and the bottom 17 of the cylinder 10 may be kept apart through the geometrical matching between the circumferential plate 32 and the sloped guide surface B1, which may also be achieved in the following manner. In this embodiment, the fat screening device 1 further includes a support 40. The support 40 includes at least one support rib 41 (includes four support ribs herein, but the instant disclosure is not limited thereto). The support ribs 41 may be integrally formed or spliced together and are caused to extend from the bottom surface of the filter mesh 30 and abut against the bottom 17 of the cylinder 10, thereby keeping the filter mesh 30 spaced apart from the bottom 17 by the distance d. A spacing 14A is formed between the filter mesh 30 and the bottom 17 of the cylinder 10, thereby improving the drainage efficiency of the fat screening device 1. In addition, one ends of the support ribs 41 intersect at the second assembling portion 34 of the filter mesh 30, and the other ends are connected to the circumferential plate 32, and the support ribs 41 are arranged in equal proportions to each other, so that structural stability between the filter mesh 30 and the cylinder 10 can be increased.

In some embodiments, the support ribs 41 may also have a short-strip shape. For example, sizes of the support ribs 41 having the short-strip shape in a radial direction of the filter mesh 30 are less than a quarter of a diameter of the filter mesh 30. In this way, a flow range of the water A1 blocked by the support 40 can be reduced, thereby ensuring the drainage efficiency of the fat screening device 1. Alternatively, the number of the support ribs 41 may be increased to ensure structural stability of the filter mesh 30, which depends on usage requirements. In some embodiments, the filter mesh 30 may be spaced apart from the bottom 17 of the cylinder 10 by the distance d through only the circumferential plate 32 or only the support 40.

Referring to FIG. 1 to FIG. 5, in this embodiment, the filter mesh 30 is further provided with a plurality of reinforcing ribs 31. The plurality of reinforcing ribs 31 include a plurality of elongated reinforcing ribs 31A and a plurality of annular reinforcing ribs 31B. The elongated reinforcing ribs 31A are arranged between the support ribs 41, and the annular reinforcing ribs 31B are connected between the support ribs 41 and penetrate the elongated reinforcing ribs 31A, thereby increasing the rigidity of the filter mesh 30. In addition, since a thickness of each of the reinforcing rib 31 is less than a thickness of each of the support ribs 41 (the thickness is defined as a size of the element in a direction from the filter mesh 30 to the cylinder 10), flowing of the water A1 is not completely blocked by the reinforcing ribs 31, thereby ensuring the drainage of the fat screening device 1. In some embodiments, the filter mesh 30 may alternatively be provided with only one reinforcing rib 31. For example, if stress concentration is likely to occur at the center of the filter mesh 30, one reinforcing rib 31 is provided to pass through the center of the filter mesh 30 to achieve an effect of reinforcement.

The fat screening device 1 in this embodiment has two drain paths. One of the drain paths is shown in FIG. 4. In FIG. 4, the water A1 flows into the accommodating space 14 of the cylinder 10 through the feed inlet 11, and is discharged out of the cylinder 10 through the bottom water outlet 13, that is, the cylinder 10 has a single drain path consisting of the feed inlet 11, the accommodating space 14, and the bottom water outlet 13.

For the other of the drain paths, refer to FIG. 1 and FIG. 5 together. In this embodiment, a lateral water outlet 18 is provided on the side wall 16 of the cylinder 10. The lateral water outlet 18 is close to or abuts against the bottom 17 of the cylinder 10. In addition, the bottom water outlet 13 is disposed at the bottom 17 of the cylinder 10, and the filter mesh 30 covers the bottom water outlet 13. In this way, most of the water A1 is first discharged through the lateral water outlet 18 through a lateral drain path, and then a remaining part of the water A1 is drained out of the cylinder 10 via the bottom water outlet 13 through a bottom drain path.

According to the above structure, when a lateral valve 61 in a lateral drain pipe 60 in communication with the lateral water outlet 18 is turned on and a bottom valve 51 in a bottom drain pipe 50 in communication with the bottom water outlet 13 is turned off, the lateral drain path is formed. Specifically, the mixture A enters the accommodating space 14 of the cylinder 10 through the feed inlet 11, and the water A1 is separated from the fat A2 by gravity and is drained out of the cylinder 10 through the lateral water outlet 18. On the contrary, when the lateral valve 61 in the lateral drain pipe 60 in communication with the lateral water outlet 18 is turned off and the bottom valve 51 in the bottom drain pipe 50 in communication with the bottom water outlet 13 is turned on, the bottom drain path is formed. Specifically, the mixture A enters the accommodating space 14 of the cylinder 10 through the feed inlet 11, and the water A1 is separated from the fat A2 by gravity and is drained out of the cylinder 10 through the bottom water outlet 13. In this embodiment, when the interface A12 where the fat A2 and the water A1 intersect gradually drops to an upper edge of an opening of the lateral water outlet 18 as an amount of the water A1 decreases, the lateral valve 61 is turned off and the bottom valve 51 is turned on to prevent the fat A2 from being drained out of the cylinder 10 through the lateral water outlet 18. In this case, the water A1 is drained out of the cylinder 10 through the bottom water outlet 13 instead, but the fat A2 is retained in the accommodating space 14 by the filter mesh 30 to collect fat A2 with high quality and high concentration.

Referring to FIG. 1, FIG. 2, and FIG. 5, in addition, in order to improve sucking efficiency and space utilization, in this embodiment, the fat screening device 1 further includes an annular base 70. The annular base 70 extends from a periphery of the bottom 17 of the cylinder 10. The annular base 70 and the cylinder 10 may be integrally formed or may be spliced together. A bent pipe T is provided in the annular base 70. The bent pipe T and the cylinder 10 may be integrally formed, or may be assembled together. Therefore, during operations such as replacing, repairing, or maintaining the bent pipe T, operators may perform operations on the bent pipe T inside the annular base 70, thereby improving operating convenience. In addition, since the bent pipe T is provided within the annular base 70, the bent pipe T can be protected by the annular base 70 from external hazards such as impact, corrosion by hydrochloric acid, or the like.

In this embodiment, one side of the annular base 70 is further provided with an opening 71, and the bent pipe T includes a vertical pipe T1 and a horizontal pipe T2 connected to the vertical pipe T1. The vertical pipe T1 is connected to the bottom water outlet 13. The horizontal pipe T2 extends toward the opening 71 and is connected to one end of the bottom drain pipe 50. The other end of the bottom drain pipe 50 and the other end of the lateral drain pipe 60 are respectively connected to a vacuum pump P2 and a vacuum pump P3 to increase a suction speed. Therefore, the horizontal pipe T2 of the bent pipe T extends toward the opening 71, so that an external pipeline can be connected to the horizontal pipe T2 through the opening 71 from one side of the cylinder 10, so that the fat screening device 1 can be supported by and fixed to an external object through a bottom of the annular base 70 of the fat screening device.

In this embodiment, the lateral water outlet 18 and the opening 71 are further located on the same side of the cylinder 10. Therefore, the vacuum pump P2 and the vacuum pump P3 can be located on the same side, thereby improving utilization efficiency of a mounting space. In some embodiments, the other end of the bottom drain pipe 50 and the other end of the lateral drain pipe 60 may also be connected to a syringe and a vacuum pump or a combination thereof. If the syringe is used for suction, the suction speed can be fine-tuned for precisely controlling an amount of sucked water. Alternatively, the other end of the bottom drain pipe 50 and the other end of the lateral drain pipe 60 may also be selectively connected to only the vacuum pump P2, the vacuum pump P3, or neither, so as to save a used space of a device. In other embodiments, the lateral water outlet 18 and the opening 71 may also be located on two opposite sides of the cylinder 10 or the lateral water outlet 18 and the opening 71 are located on different sides, for example, the two are at 90 degrees or 60 degrees with respect to each other, which depends on usage requirements. Based on the above, some embodiments of the instant disclosure provide a fat screening device 1, which effectively improves quality and a survival rate of collected fat A2 through a gravity separation principle and screening of the cylinder 10 and the sieve basket 20, and is adapted for separating and collecting fat cells with a high survival rate from living tissues for fat transplantation. In addition, most of the water A1 may be first drained out of the cylinder 10 via the lateral water outlet 18 through the lateral drain path, and then a remaining part of the water A1 is drained out of the cylinder 10 via the bottom water outlet 13 through the bottom drain path. With the filter mesh 30 covering the bottom water outlet 13, fat A2 with high quality and high concentration is collected. The instant disclosure has numerous functions and advantages as described above.

Although the instant disclosure has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A fat screening device, comprising:
a cylinder comprising a feed inlet, an air outlet, a bottom water outlet, and an accommodating space that is in communication with the feed inlet, the air outlet, and the bottom water outlet, wherein the feed inlet is configured to receive a mixture, the bottom water outlet is disposed at a bottom of the cylinder, the accommodating space is configured to accommodate water and fat resulting from automatic stratification, by gravity, of the mixture after storage in the accommodating space, and the bottom water outlet is configured to discharge the water;
a sieve basket covering the feed inlet, arranged separately from the air outlet, and configured to screen the mixture to discharge the water and the fat into the accommodating space;
a filter mesh disposed in the accommodating space, spaced apart from the bottom by a distance, and covering the bottom water outlet of the cylinder; and
an annular base, wherein the annular base extends from a periphery of the bottom, a side of the annular base is provided with an opening, a bent pipe is provided in the annular base, the bent pipe comprises a vertical pipe and a horizontal pipe connected to the vertical pipe, the vertical pipe is connected to the bottom water outlet, and the horizontal pipe extends toward the opening.

2. The fat screening device according to claim 1, wherein a size of a plurality of filter holes of the filter mesh ranges from 100 μm to 400 μm.

3. The fat screening device according to claim 1, further comprising a support, wherein the support is connected between the filter mesh and the bottom to keep the filter mesh spaced apart from the bottom by the distance.

4. The fat screening device according to claim 3, wherein the support comprises at least one support rib, and the support rib extends from a bottom surface of the filter mesh and abuts against the bottom.

5. The fat screening device according to claim 1, wherein the filter mesh is provided with at least one reinforcing rib.

6. The fat screening device according to claim 1, wherein the filter mesh comprises a circumferential plate and a filter area located within the circumferential plate, and the circumferential plate is fixed to the cylinder.

7. The fat screening device according to claim 6, wherein a guide block protrudes from a periphery of the bottom, the guide block has a sloped guide surface, and the circumferential plate abuts against and is fixed to the guide block to keep the filter mesh spaced apart from the bottom by the distance.

8. The fat screening device according to claim 1, wherein the cylinder comprises a lateral water outlet, and the lateral water outlet is located on the same side of the cylinder as the opening.

9. The fat screening device according to claim 1, wherein a first assembling portion is provided at the bottom of the cylinder, the first assembling portion is located around the bottom water outlet, a second assembling portion is provided on a bottom surface of the filter mesh, and the second assembling portion is correspondingly assembled to the first assembling portion.

10. The fat screening device according to claim 9, wherein the first assembling portion is an annular buckling groove, and the second assembling portion comprises a plurality of buckling claws arranged annularly.

11. A fat screening device, comprising:
a cylinder comprising a feed inlet, an air outlet, a bottom water outlet, and an accommodating space that is in communication with the feed inlet, the air outlet, and the bottom water outlet, wherein the feed inlet is configured to receive a mixture, the bottom water outlet is disposed at a bottom of the cylinder, the accommodating space is configured to accommodate water and fat resulting from automatic stratification, by gravity, of the mixture after storage in the accommodating space, and the bottom water outlet is configured to discharge the water; and a sieve basket covering the feed inlet, arranged separately from the air outlet, and configured to screen the mixture to discharge the water and the fat into the accommodating space;

wherein the cylinder further comprises a lateral water outlet disposed on a side wall of the cylinder, and the lateral water outlet is close to the bottom of the cylinder and is configured to discharge the water.

12. The fat screening device according to claim 11, further comprising a lateral drain pipe in communication with the lateral water outlet of the cylinder, wherein the lateral drain pipe has a lateral valve.

13. A fat screening device, comprising:

a cylinder comprising a feed inlet, an air outlet, a bottom water outlet, and an accommodating space that is in communication with the feed inlet, the air outlet, and the bottom water outlet, wherein the feed inlet is configured to receive a mixture, the bottom water outlet is disposed at a bottom of the cylinder, the accommodating space is configured to accommodate water and fat resulting from automatic stratification, by gravity, of the mixture after storage in the accommodating space, and the bottom water outlet is configured to discharge the water;

a sieve basket covering the feed inlet, arranged separately from the air outlet, and configured to screen the mixture to discharge the water and the fat into the accommodating space; and a bottom drain pipe in communication with the bottom water outlet of the cylinder, wherein the bottom drain pipe has a bottom valve.

14. The fat screening device according to claim 1, wherein a plurality of sieve openings are provided on a lateral surface and a bottom surface of the sieve basket.

15. The fat screening device according to claim 1, wherein a size of a plurality of sieve openings of the sieve basket ranges from 1 mm to 4 mm.

16. The fat screening device according to claim 1, wherein the feed inlet and the air outlet of the cylinder are disposed on a top of the cylinder.

17. The fat screening device according to claim 1, further comprising a vacuum pump that is in communication with the air outlet of the cylinder.

* * * * *